United States Patent [19]

Tsezos et al.

[11] Patent Number: 4,828,882
[45] Date of Patent: May 9, 1989

[54] PARTICLE ENCAPSULATION TECHNIQUE

[75] Inventors: Marios Tsezos, Toronto; Soo H. Noh, Hamilton, both of Canada

[73] Assignee: Canadian Patents & Developments Limited, Ontario, Canada

[21] Appl. No.: 26,713

[22] Filed: Mar. 16, 1987

[51] Int. Cl.$^4$ ............................................. B05D 1/22
[52] U.S. Cl. ................................ 427/213; 427/352; 427/353
[58] Field of Search ..................... 427/213, 352, 353

[56] References Cited

U.S. PATENT DOCUMENTS

| | | | |
|---|---|---|---|
| 2,809,900 | 10/1957 | Sarbach | 427/353 X |
| 2,983,960 | 5/1961 | Jilge | 427/353 X |
| 4,259,445 | 3/1981 | Glass et al. | 435/178 |
| 4,337,313 | 6/1982 | Hershberger et al. | 435/177 |
| 4,350,675 | 9/1982 | Drake | 424/1 |
| 4,391,909 | 7/1983 | Lim | 435/178 |
| 4,428,973 | 1/1984 | Horner et al. | 427/213 X |
| 4,438,198 | 3/1984 | Schmer | 435/178 |
| 4,518,693 | 5/1985 | Kuu | 435/178 |
| 4,621,072 | 11/1986 | Arntz | 427/213 |
| 4,701,353 | 10/1987 | Mutsers et al. | 427/213 |

FOREIGN PATENT DOCUMENTS

| | | |
|---|---|---|
| 544029 | 7/1957 | Canada . |
| 754504 | 3/1967 | Canada . |
| 795279 | 9/1968 | Canada . |
| 797153 | 10/1968 | Canada . |
| 808109 | 3/1969 | Canada . |
| 982941 | 2/1976 | Canada . |
| 1049334 | 2/1979 | Canada . |
| 1087933 | 10/1980 | Canada . |
| 1132048 | 9/1982 | Canada . |

Primary Examiner—Shrive Beck
Attorney, Agent, or Firm—Mason, Fenwick & Lawrence

[57] ABSTRACT

A process whereby particulate materials with a polymeric coating of controlled thickness are obtained by passing gas at a pre-determined temperature and flow rate substantially symmetrically through a bed of particles to create a coherent symmetrical spouting zone of fully-spouted, suspended particles is disclosed. The suspended particles are contacted with an atomized spray of polymer solution. The spray has a controlled flow rate and is confined to the spouting zone. As the process proceeds, the solvent evaporates from the fine droplets of the polymer solvent solution on contact or very quickly after contact of the polymer solvent solution with the particles. Structurally sensitive particulate material such as biomass is therefore only fleetingly contacted with solvent, on its outer shell only, and no substantial damage to the material can be effected by the solvent. Also, the coating solidifies quickly so that the little or no particle agglomeration or attrition occurs. The coating can be made porous by incorporating a leachable additive into the polymer solution and contacting the particles subsequent to coating with a solvent to dissolve the additive.

7 Claims, 1 Drawing Sheet

PARTICLE ENCAPSULATION TECHNIQUE

BACKGROUND OF THE INVENTION

This invention relates to processes of coating particulate materials.

It is known to provide a pharmaceutical product such as antibiotics and other forms of pills with a coating of some type, e.g., enteric coatings so that the medicine may pass through the stomach and treat the lower intestines and bowel, and other sparingly soluble coatings to allow for controlled and delayed release of the drug into the body. It is also known to coat carbon particles, for medical applications. Yuichi Mori et al "Permeability of heparinized hydrophilic polymer (HRDS): Application to semipermeable membrane for microencapsulation of activated carbon" J. biomedical Material Research, Vol. 16, 27-30, 1982; Chang T. M. S. "Hemoperfusion over microencapsulated absorbent in a patient with hepatic coma", Lancet, ii, 1371-1372, 1972; and Chang T. M. S., Espinosa-Melendaz, E., Francoeur, T. E. and Eade, N. R. "Albumin-collodion activated coated charcoal hemoperfusion in the treatment of severe theophylline intoxication in a 3-year old patent" Pediatric, 65, 811-814, 1980 relate to carbon encapsulation for medical purposes.

Fluidized bed systems have previously been used to coat particles as disclosed in Canadian Pat. Nos. 1,049,334 (Worts et al); 808,109 (Kaltenbach); 754,504 (Grass et al); 544,029 (Tadema et al); and 797,153 (Lindolf et al). These systems generally have the disadvantages of providing non-uniform coatings of unpredictable thickness and of providing an unsatisfactory level of particle agglomeration.

Canadian Pat. No. 795,279 (Heiser) describes a system wherein a high velocity jet is applied to a bed of particles to create an asymmetrical zone of moving particles. A nozzle to apply coating solution to the particles is located below the particle bed and thus may not only contact particles in the moving particle zone. Product particles obtained from this system would be unevenly coated and would probably still have a high degree of agglomeration.

SUMMARY OF THE INVENTION

It is an object of the present invention to provide a process for coating particulate materials which obviates or mitigates the above-mentioned disadvantages.

Accordingly, the invention provides a process to provide particulate materials with a polymeric coating of controlled thickness. Gas is passed at a pre-determined temperature and flow rate substantially symmetrically through a bed of particles to create a coherent, symmetrical spouting zone of suspended, fully-spouted particles. The suspended particles are contacted with an atomized spray of polymer solution. The spray has a controlled flow rate nd is confined to the spouting zone. As the process proceeds, the solvent evaporates from the fine droplets of polymer solvent solution on contact or very quickly after contact of the polymer solvent solution with the target particles. Structurally sensitive target particulate material such as biomass is therefore only fleetingly contacted with the solvent, on its outer shell only and no substantial damage to the material can be effected by the solvent. Also, the coating solidifies quickly so that little or no particle agglomeration occurs.

When it is desired to obtain a porous coating, a leachable additive or mixture of leachable additives is added to the polymer solution prior to spraying. After the particles are coated, they are contacted with a solvent or a mixture of solvents suitable for dissolving the leachable additive to provide pores in the polymer coating. The pore size and porosity of the coating is advantageously controlled by controlling the type and concentration of additive in the polymer solution.

Although the process is suitable for particulate material in general, the process of the invention is particularly advantageously applied to biomass particles. These are known in the prior art to be useful adsorptive materials, displaying a high degree of selectivity of the material they will adsorb. For them to be effective, the physical and chemical cell architecture of the biomass should be maintained intact, as far as possible. Damage thereto should be minimized. Useful types of biomass include that obtained as sludge from water treatment plants, and that obtained as industrial fermentation waste. They are normally difficult to handle, since they lack physical strength and are small. They are made up of individual microorganism cells, which may be bacterial cells, fungal cells, etc., probably non-functioning as cells. The process of the present invention retains their adsorptive properties whilst increasing the particle size and greatly enhancing their mechanical strength, by providing them with a thin polymer membrane coating or encapsulation. The polymer membrane is of controlled porosity so that the biomass can contact solutions to be treated.

In the process of the invention, it is important that the encapsulated particles be substantially prevented from coalescing with one another. As originally applied, as the solvent evaporates, the polymeric coating will be sticky. Coalescence of particles is prevented by applying a uniform, thin coating of polymer solution which is achieved by applying the coating in the spouting zone. Also, proper control of the drying rate of the particles after coating will further reduce agglomeration and ensure that the solvent does not evaporate too quickly on the surface of the particle which could result in a discontinuous, non-uniform coating. The heat applied to the particles in the process of the present invention is accurately controlled through the use of a coherent spouting zone. Heating control is achieved by controlling the temperature of the inlet air accompanying the polymer solution to form the spouting zone.

Uniform symmetrical circulation of particles is required to produce uniform coating of particles. This is provided by using a coherent symmetrical spouting region.

The coating thickness is directly proportional to the concentration of the polymer in the solution and its spraying rate and time. The amount of coating materials applied to each particle is as low as possible, but should be sufficient to provide adequate structural strength. Preferably, not less than 1% by weight of coating should be applied.

BRIEF DESCRIPTION OF THE DRAWING

The invention will now be described with reference to FIG. 1 which is a diagrammatic cross-section of a spouting bed system.

DESCRIPTION OF THE PREFERRED EMBODIMENTS

Figure 1:
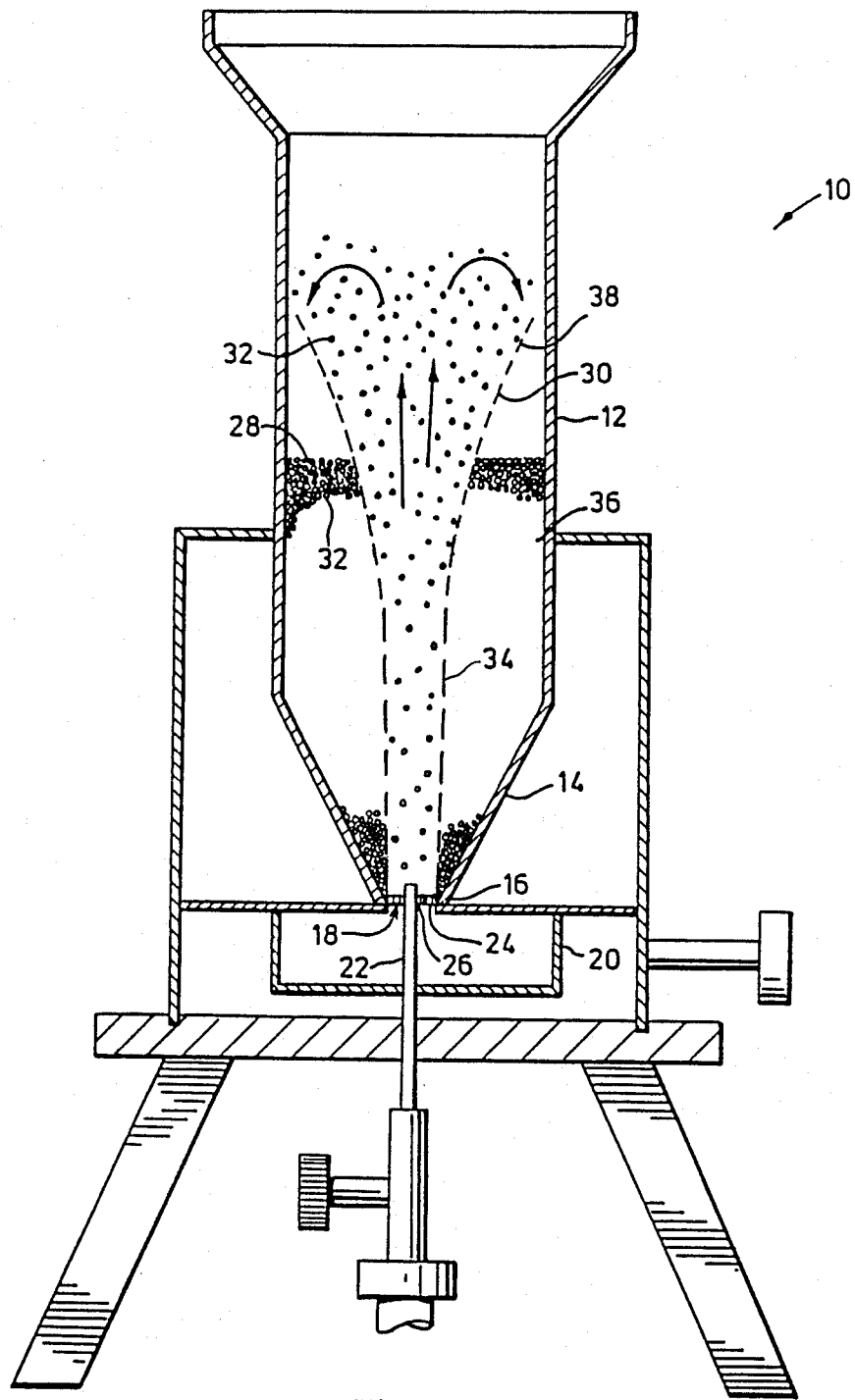

As can be seen in this figure, the system 10 consists of a generally cylindrical container 12 having an inverted frustoconical lower end 14. This lower end 14 is open at its base 16 to provide an inlet orifice 18. Connected to the base of the container 12 is an air chamber 20. Within this chamber 20 is a nozzle 22 which extends past the orifice 18 into the container. A screen 24 is located over the orifice 18 with an opening 26 to accommodate the nozzle 22.

In operation, particles 32 are charged into the container to form a bed 28. Heated suspension air from an outside source is then passed into the chamber 20 and from there passes into the bed 28. Due to the configuration of the container 12, a symmetrical, coherent fountain or spout 30 of particles 32 is obtained. When the system reaches thermal equilibrium, polymer solution with leachable material mixed therein is then passed through the nozzle 22 and the solution is sprayed directly into the spout 30. Polymer particles 32 in the lower end 34 of the spout are thereby evenly coated, and are quickly dried by the suspension air to reduce potential damage to the particles and reduce agglomeration of the particles. When the particles reach the top of the spout 38 they drop down the sides 36 of the container 12 to the base 16 of the container for return and recycle to the spout 30.

During the process, the inlet and outlet temperatures of the system are continuously monitored. The inlet temperature is in the range of 0°–120°.

Generally, the overall coating period can range from 5–120 minutes, preferably 10–60 minutes depending on the operating variables including particle charge, spray rate, and the total coating solution volume sprayed. When the desired amount of coating has been applied to the particles, the spraying nozzle is shut off and the particles are dried further by the suspension air. When the particles are sufficiently dried, the suspension air flow is stopped and the coated particles are recovered.

The particles are then intimately mixed with solvent under appropriate pH conditions to dissolve the leachable material and obtain a network of pores in the coating.

The temperature of the air is sufficient to evaporate the solvent and the polymer substantially on contact. Preferably, the inlet temperature is in the range of 0°–200° C. and most preferably at 0°–120° C.

Particles suitably coated by the process of the present invention include granulated live or dead biomass particles, activated carbon particles, ion exchange resin particles, granulated natural absorbents, granulated synthetic adsorbents, granulated enzymes, granulated chemicals and pharmaceuticals. Preferably, the particles are biomass particles. The particles are suitably in the range of 0.1–20 mm in diameter, and most suitably 0.2–5 mm in diameter.

The polymers suitably used in the invention include cellulose derivatives including cellulose acetate, cellulose triacetate, methyl cellulose, ethyl cellulose, carboxymethyl cellulose, cellulose acetate phthalate, cellulose propionate morpholinobutyrate; polysulfone, polyvinylchloride, polyvinyl formal, polyformaldehyde, polystyrene, polycarbonate, polyurethane, copolymer of acrylonitrile and vinylchloride; polyvinylidene chloride, polymethyl methacrylate, polybutyl methacrylate; polyacrylonitriles, polyvinylacetate, polyvinylpyrrolidene, polyvinylalcohol, polyamide, polyimide, polyether sulfone, polyvinyl butyrals and mixtures thereof.

The solvents used to dissolve the polymers should dissolve readily the chosen polymer or mixture of polymers and evaporate within the temperature of operation. Suitable solvents include acetone, alcohols, tetrahydrofuran, dimethylformamide, M-pyrol, dimethylacetamide, Gamma-butyrolactone, pyridine, dioxane, cyclohexanone, cellusolves, and mixtures thereof.

The polymer solution preferably has a viscosity of less than 500 cp, and most preferably less than 100 cp. Preferably the particles are coated with a polymer coating that is as thin as possible, but which is sufficiently thick to provide adequate structural strength. Preferably, the amount of coating used is at least 1% of the weight of the particle, and most preferably at least 5%.

To obtain a porous coating, a leachable additive or mixture of leachable additives are added to the coating prior to the spraying. The leachable additive is suitably selected from salts such as chlorides, nitrates, carbonates, i.e.—calcium carbonate, calcium chloride, sodium chloride, sodium carbonate, sodium bicarbonate, zinc chloride, and soluble organic matter such as glucose, sugars, dextran, polyethylene glycol, polyvinylpyrrolidene, polyvinyl alcohol.

The appropriate air flow rates and coating spraying rates for a given size of bed can readily be determined by one skilled in the art.

The invention will now be described with reference to the following example.

EXAMPLE 1

The invention was carried out using the apparatus of FIG. 1, with the following dimensions:
Cylindrical Container Diameter: $D_C = 52$ mm
Inlet Opening Diameter: $D_I/D_C = 0.144$
Frustoconical Lower End Angle = 40°

A polymer solution of 6.5% by weight polyvinylformal dissolved in 76.5% by weight tetrahydrofuran with 17% by weight glucose of an average diameter of 15 mm suspended therein was provided.

Particles of biomass, 14/30 U.S. standard mesh in diameter were used.

The process was carried out as described in the description of the preferred embodiment using the following process conditions:

| | |
|---|---|
| Suspension Air Flow | 400 mL/sec |
| Atomizer Air Fow | 86 mL/sec |
| Suspension Air Inlet Temperature | 80°C. |
| Coating Solution Spraying Rate | 3.0 mL/min |
| Particles Charged | 40 g |
| Viscosity of Coating Solution | 50 cp |
| Particle Size of Particulate Material | 14/30 mm (U.S. standard mesh) |

The particles were then recovered and mixed with water to dissolve the glucose under pH conditions of pH 7.0.

Substantially non-agglomerated polymer particles having uniform coatings of uniform thickness and porosity were obtained.

We claim:

1. A process to provide particulate material with a polymer coating of controlled thickness comprising the steps of:
passing gas at a predetermined temperature and flow rate substantially symmetrically through a bed of particles to create a coherent spouting zone of suspended particles;

contacting said suspended particles with an atomized spray of polymer solution, said polymer solution containing at least one leachable additive;

said spray having a controlled flow rate and being confined to said spouting zone to provide even coating of controlled thickness on said particles; and contacting said particles after coating with solvent suitable for dissolving said additive to provide a porous coating.

2. The process of claim 1 wherein the inlet temperature of said gas is in the range of 0°–200° C.

3. The process of claim 2 wherein the inlet temperature of said gas is in the range of 0°–120° C.

4. The process of claim 1 wherein said leachable additive is selected from metallic salts and soluble organic matter.

5. The process of claim 4 wherein said leachable additive is selected from chlorides, nitrates and carbonates.

6. The process of claim 4 wherein said leachable additive is selected from calcium carbonate, sodium carbonate, sodium bicarbonate, calcium chloride and zinc chloride.

7. The process of claim 4 wherein said soluble organic matter is selected from glucose, sugars, dextran, polyethylene glycol, polyvinylpyrrolidene and polyvinyl alcohol.

* * * * *